US00PP37183P2

(12) United States Plant Patent
Arts

(10) Patent No.: US PP37,183 P2
(45) Date of Patent: Dec. 30, 2025

(54) BLUEBERRY PLANT NAMED 'FV2401'

(50) Latin Name: *Vaccinium corymbosum*
Varietal Denomination: FV2401

(71) Applicant: FV B.V., De Kwakel (NL)

(72) Inventor: Niels Arts, Aalsmeer (NL)

(73) Assignee: FV B.V., De Kwakel (NL)

( * ) Notice: Subject to any disclaimer, the term of this patent is extended or adjusted under 35 U.S.C. 154(b) by 0 days.

(21) Appl. No.: 19/259,523

(22) Filed: Jul. 3, 2025

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of Blueberry plant named 'FV2401', characterized by its semi-upright and bushy plant habit with a narrow crown; freely branching habit; mid-season fruiting variety; high fruit yield within a narrow harvest window; homogenous large and high quality dark blue-colored spherical fruits; high fruit picking efficiency due to narrow plant crown, homogenous large fruit size and narrow harvest period; and good fruit postharvest longevity.

4 Drawing Sheets

Figure 1:
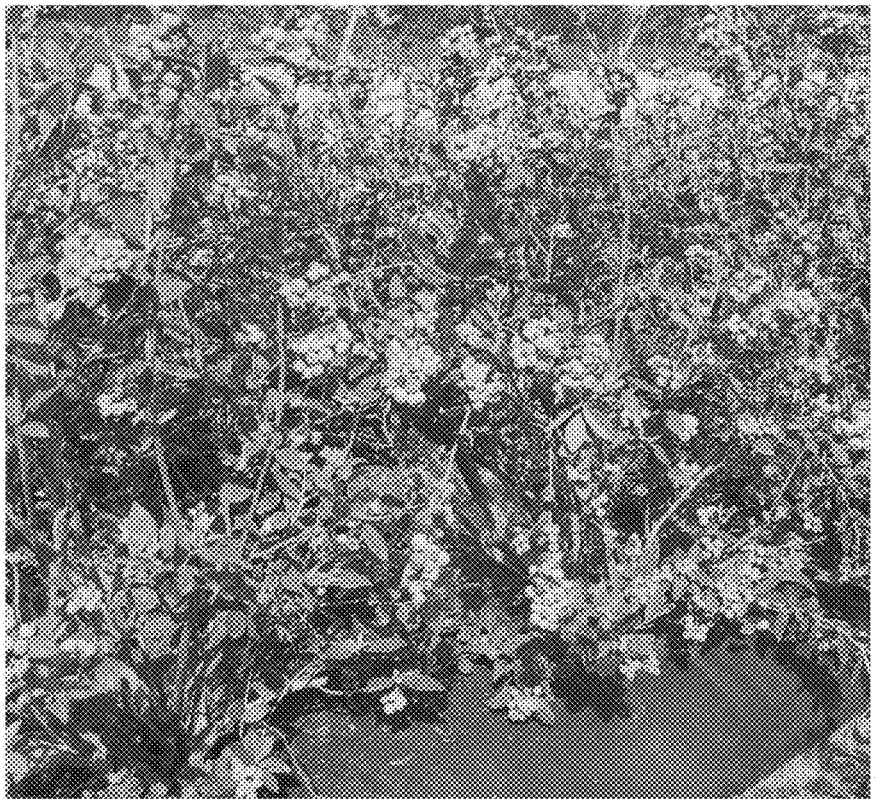

Botanical designation: *Vaccinium corymbosum.*
Cultivar denomination: 'FV2401'.

CROSS-REFERENCED TO PRIOR-FILED APPLICATIONS

A European Community Plant Breeder's Rights application for the instant plant was filed by the Applicant/Assignee, FV B.V. of De Kwakel, The Netherlands on Sep. 18, 2024, application number 2024/2171. Foreign priority is not claimed to this application.

BACKGROUND OF THE INVENTION

The present Invention relates to a new and distinct cultivar of Blueberry plant, commonly referred to as Highbush Blueberry, botanically known as *Vaccinium corymbosum* and hereinafter referred to by the name 'FV2401'.

The new Blueberry plant is a product of a planned breeding program conducted by the Inventor in De Kwakel, The Netherlands and Lepe, Huelva, Spain. The objective of the breeding program was to develop new early-fruiting Blueberry plants with large fruits and good fruit quality, productivity, uniformity and postproduction longevity.

The new Blueberry plant originated from a cross-pollination by the Inventor during the spring of 2015 in De Kwakel, The Netherlands of *Vaccinium corymbosum* 'Camellia', disclosed in U.S. Plant Pat. No. 18,151, as the female, or seed, parent with *Vaccinium corymbosum* 'Snowchaser' disclosed in U.S. Plant Pat. No. 19,503, as the male, or pollen, parent. The new Blueberry plant was discovered and selected by the Inventor as a single plant from within the progeny of the stated cross-pollination in a controlled environment in Lepe, Huelva, Spain in March 2017.

Asexual reproduction of the new Blueberry plant by stem cuttings in a controlled environment at Lepe, Huelva, Spain since June 2017 has shown that the unique features of this new Blueberry plant are stable and reproduced true to type in successive generations of asexual reproduction.

SUMMARY OF THE INVENTION

Plants of the new Blueberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'FV2401'. These characteristics in combination distinguish 'FV2401' as a new and distinct Blueberry plant:

1. Semi-upright and bushy plant habit with a narrow crown.
2. Freely branching habit.
3. Mid-season fruiting variety.
4. High fruit yield within a narrow harvest window.
5. Homogenous large and high quality dark blue-colored spherical fruits.
6. High fruit picking efficiency due to narrow plant crown, homogenous large fruit size and narrow harvest period.
7. Good fruit postharvest longevity.

Plants of the new Blueberry differ primarily from plants of the female parent, 'Camellia', in the following characteristics:

1. Plants of the new Blueberry are not as upright as plants of 'Camellia'.
2. Plants of the new Blueberry are not as vigorous as plants of 'Camellia'.
3. Plants of the new Blueberry produce fruit earlier than plants of 'Camellia'.
4. Fruits of plants of the new Blueberry have larger calyces than fruits of plants of 'Camellia'.

Plants of the new Blueberry differ primarily from plants of the male parent, 'Snowchaser', in the following characteristics:

1. Plants of the new Blueberry are more vigorous than plants of 'Snowchaser'.
2. Plants of the new Blueberry produce fruit later than plants of 'Snowchaser'.
3. Plants of the new Blueberry produce larger fruit than plants of 'Snowchaser'.
4. Plants of the new Blueberry do not produce any "red-back fruits" whereas plants of 'Snowchaser' produce "red-back fruits".

Plants of the new Blueberry can also be compared to plants of *Vaccinium corymbosum* 'FV1907', disclosed in U.S. Plant Pat. No. 34,084. In side-by-side comparisons, plants of the new Blueberry differ from plants of 'FV1907' in the following characteristics:

1. Plants of the new Blueberry are more upright than plants of 'FV1907'.
2. Plants of the new Blueberry flower later than plants of 'FV1907'.
3. Sepals of plants of the new Blueberry are darker green in color than sepals of plants of 'FV1907'.
4. Plants of the new Blueberry produce fruit during the mid-season whereas plants of 'FV1907' produce fruit during the early season.
5. Plants of the new Blueberry produce larger, more rounded and heavier fruits than plants of 'FV1907'.

BRIEF DESCRIPTION OF THE PHOTOGRAPHS

The accompanying colored photographs illustrate the appearance of the new Blueberry plant showing the colors as true as it is reasonably possible to obtain in colored reproductions of this type. Colors in the photographs may differ slightly from the color values cited in the detailed botanical description which accurately describe the colors of the new Blueberry plant.

The photograph on the first sheet (FIG. 1) is a side perspective view of typical flowering plants of 'FV2401'.

Figure 2:
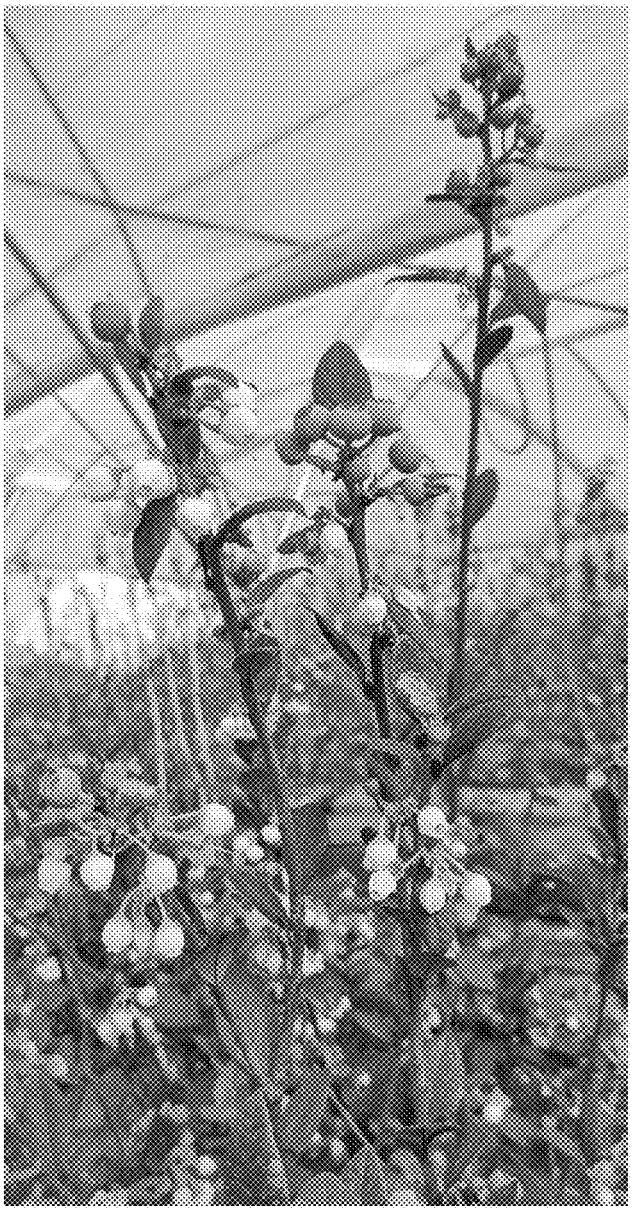

The photograph on the second sheet (FIG. 2) is a close-up view of typical flowers and fruits of 'FV2401'.

Figure 3:
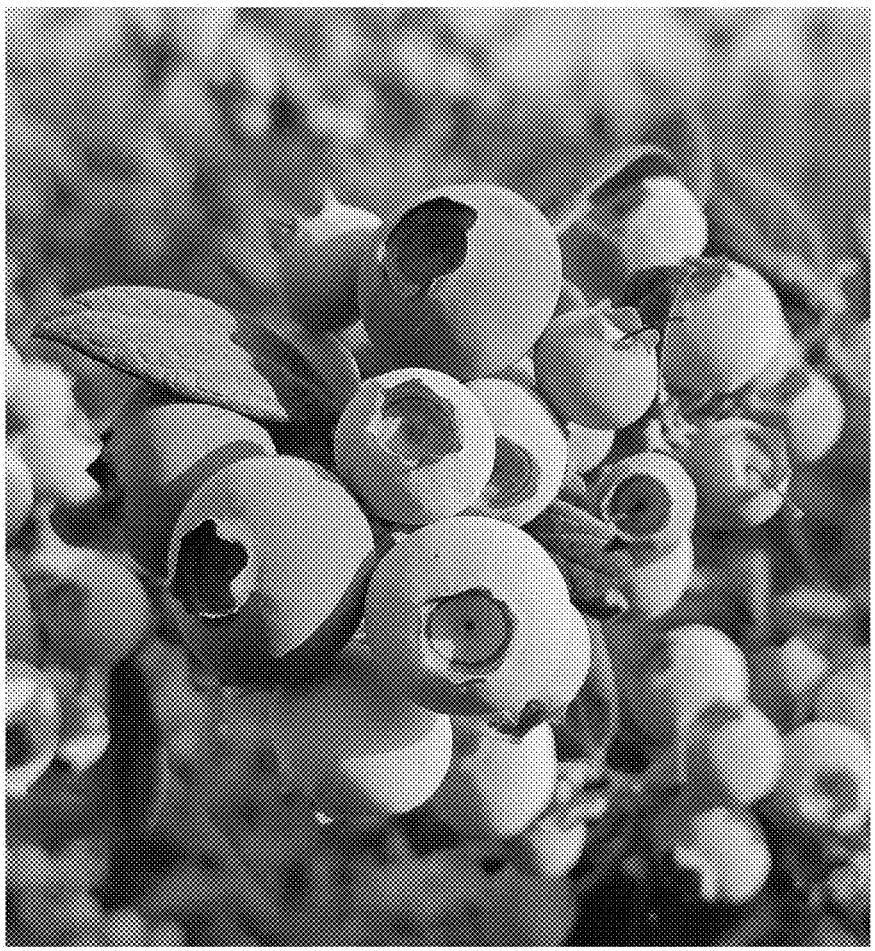

The photograph on the third sheet (FIG. 3) is a close-up view of typical developing and developed fruits of 'FV2401'.

Figure 4:
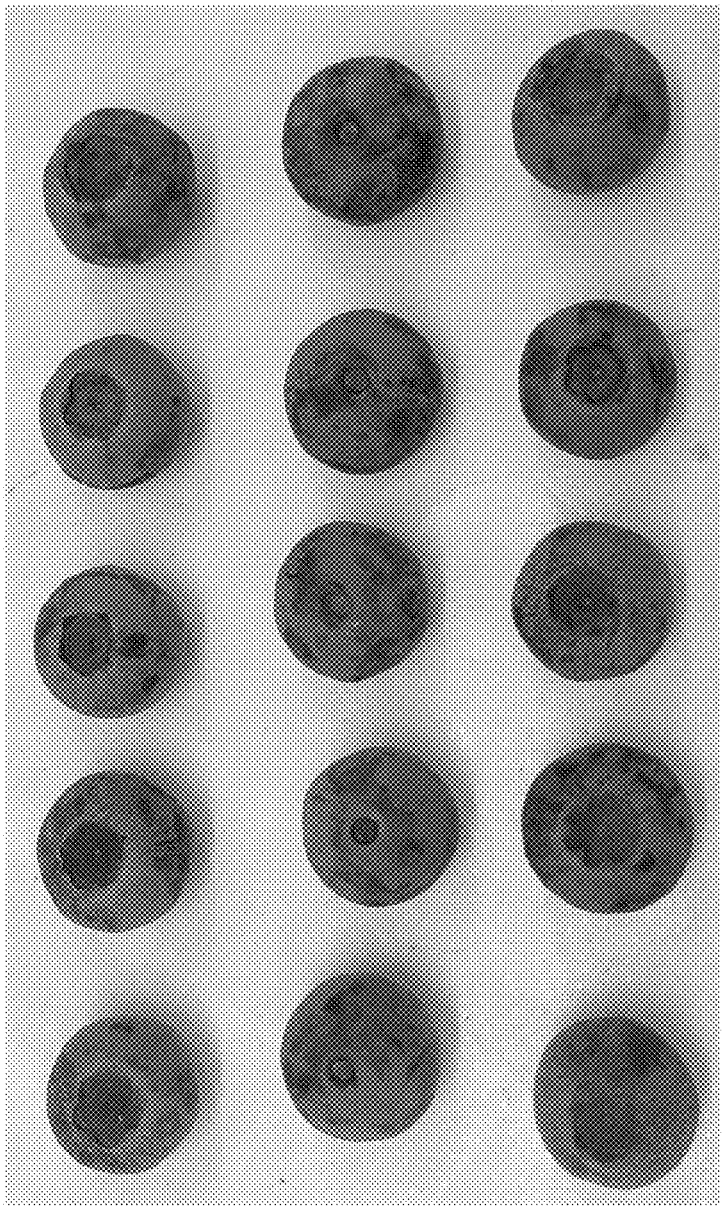

The photograph on the fourth sheet (FIG. 4) is a close-up view of typical developed fruits of 'FV2401'.

DETAILED BOTANICAL DESCRIPTION

The aforementioned photographs, following observations and measurements describe plants grown during the spring in ground beds in an outdoor nursery and polyethylene-covered greenhouse in Gibaleón, Huelva, Spain and under typical cultural practices of Blueberry plant production. During the production of the plants, day temperatures averaged 30° C. and night temperatures averaged 7° C. Plants were pinched one time and were three years old when the photographs and description were taken. In the following description, color references are made to The Royal Horticultural Society Colour Chart, 2015 Edition, except where general terms of ordinary dictionary significance are used.

Botanical classification: *Vaccinium corymbosum* 'FV2401'.

Parentage:

*Female, or seed, parent.*—*Vaccinium corymbosum* 'Camellia', disclosed in U.S. Plant Pat. No. 18,151.

*Male, or pollen, parent.*—*Vaccinium corymbosum* 'Snowchaser', disclosed in U.S. Plant Pat. No. 19,503.

Propagation:

*Type.*—By stem cuttings.

*Time to initiate roots, summer.*—About three weeks at temperatures about 26° C.

*Root description.*—Fibrous; depending on age, typically 165C and 200A in color, actual color of the roots is dependent on substrate composition, water quality, fertilizer type and formulation, substrate temperature and physiological age of roots.

*Rooting habit.*—Moderately dense.

Plant description:

*Plant and growth habit.*—Semi-upright and bushy plant habit with a narrow crown; moderately vigorous growth habit and moderate growth rate; plants produce fruit on one-year and current season's shoots; classified as a mid-season variety.

*Plant height.*—About 92 cm.

*Plant diameter.*—About 71 cm.

Branch description:

*Quantity per plant.*—About six primary branches each with about ten secondary branches each; pinching enhances branching potential.

*Length.*—About 40 cm to 60 cm.

*Diameter.*—About 4 mm.

*Internode length.*—About 2 cm.

*Strength.*—Strong.

*Aspect.*—Mostly upright.

*Texture and luster.*—Smooth, glabrous; matte.

*Color, developing.*—Close to 144C.

*Color, developed.*—Close to 178A and at the nodes, close to 187A; if woody, close to 199C.

Leaf description:

*Arrangement.*—Alternate; simple.

*Length.*—About 6 cm to 7 cm.

*Width.*—About 3 cm.

*Shape.*—Elliptic.

*Apex.*—Acute.

*Base.*—Acute.

*Margin.*—Entire.

*Texture and luster, upper surface.*—Smooth, glabrous; leaves becoming rugose with development; semi-glossy.

*Texture and luster, lower surface.*—Smooth, glabrous; matte.

*Venation.*—Pinnate and reticulate.

*Color.*—Developing leaves, upper surface: Close to 144A. Developing leaves, lower surface: Close to 146B. Fully expanded leaves, upper surface: Close to 147A; venation, close to 147B. Fully expanded leaves, lower surface: Close to 145A; venation, close to 145B.

*Petioles.*—Length: About 7 mm. Diameter: About 3 mm. Strength: Strong. Texture and luster, upper and lower surfaces: Smooth, glabrous; matte. Color: Developing leaves, upper surface: Close to 144C. Developing leaves, lower surface: Close to 59A to 59B. Fully expanded leaves, upper surface: Close to 145A tinged with close to 58A and 59A. Fully expanded leaves, lower surface: Close to 59A to 59B.

Flower description:

*Flower form and flowering habit*.—Single urceolate-shaped flowers arranged in dense panicles; freely flowering with about eight flowers per inflorescence, about 15 to 30 flowers per lateral branch and about 640 to 740 flowers developing per plant during the flowering season; flowers, drooping; flower sutures conspicuous.

*Fragrance*.—None detected.

*Natural flowering season*.—In Lepe, Huelva, Spain plants typically flower the end of January to the beginning of February; individual flowers last about one week, not persistent.

*Flower buds*.—Length: About 7 mm. Diameter: About 5 mm. Shape: Ovoid. Texture and luster: Smooth, glabrous; matte. Color: Close to 166A and 164A.

*Inflorescence height*.—About 10 cm to 20 cm.

*Inflorescence diameter*.—About 4 cm to 5 cm.

*Flower diameter*.—About 1 cm.

*Flower depth* (*height*).—About 1 cm to 1.5 cm.

*Petals*.—Arrangement: Five petals, fused. Length: About 1 cm. Width: About 1 cm. Shape: Roughly circular. Apex: Cuspidate. Margin, distal free part: Entire; undulate. Texture and luster, upper and lower surfaces: Smooth, glabrous, silky; matte. Color: When opening, upper and lower surfaces: Close to 155A tinged with close to 186B. Fully opened, upper and lower surfaces: Close to 155D; venation, close to 155D; color becoming closer to 165A with subsequent development.

*Sepals*.—Arrangement: Five sepals, fused; incurved. Calyx length: About 5 mm to 8 mm. Calyx width: About 8 mm. Length: About 5 mm to 8 mm. Width: About 3 mm. Shape: Ovate. Apex: Acute. Margin: Entire. Texture and luster, upper and lower surfaces: Smooth, glabrous, silky; matte. Color: When developing, upper and lower surfaces: Close to 138B. Fully opened, upper surface: Close to 138A. Fully opened, lower surface: Close to 144B.

*Peduncles*.—Length: About 4 mm to 10 mm. Diameter: About 4 mm. Strength: Strong. Aspect: About 45° from the lateral branch axis Texture and luster: Smooth, glabrous; matte. Color: Close to 144D.

*Pedicels* (*flowers and fruits*).—Length: About 1.2 cm. Diameter: About 1 mm. Strength: Strong. Aspect: About 45° to 90° from the peduncle axis. Texture and luster: Smooth, glabrous; slight gloss. Color: Close to 144B to 144C.

*Reproductive organs*.—Stamens: Quantity per flower: About seven to nine. Filament length: About 3 mm. Filament color: Close to 162D. Anther size: About 1 mm by 4 mm. Anther color: Close to 165A. Pollen amount: Moderate. Pollen color: Yellow. Pistils: Quantity per flower: One. Pistil length: About 1 cm. Stigma diameter: About 1 mm. Stigma shape: Pointed. Stigma color: Close to 149A. Style length: About 8 mm. Style color: Close to 149A. Ovary color: Close to 137A.

*Fruits*.—Type: Berry. Quantity: One per flower; about 1.5 to 2 kilograms of fruits are formed on one-year old plants. Time to ripening: About six days. Keeping quality: Good postproduction longevity, about two weeks. Size: Homogeneously large, about 2 cm by 2.2 cm. Weight: About 3.6 gr. Shape: Roughly spherical. Diameter of calyx basin: Medium. Depth of calyx basin: Absent or shallow. Firmness: Firm. Texture and luster: Smooth, glabrous; matte. Flesh color: Close to 144D. Skin color: Close to 103A; bloom, close to NN155A Taste: Medium sweetness; brix, close to 12%; low acidity.

*Seeds*.—Quantity: About 44 per berry. Length: About 2 mm. Diameter: About 1 mm. Texture: Smooth, glabrous. Color: Close to 167A and becoming closer to 172A.

Pathogen & pest resistance: To date, plants of the new Blueberry have been observed to be resistant to pathogens and pests common to Blueberry plants.

Temperature tolerance: Plants of the new Blueberry have been observed to tolerate temperatures ranging from about 4° C. to about 40° C. and to be suitable for USDA Hardiness Zone 9.

It is claimed:

1. A new and distinct Blueberry plant named 'FV2401' as herein illustrated and described.

* * * * *